US00PP20865P2

(12) United States Plant Patent
Bradford

(10) Patent No.: US PP20,865 P2
(45) Date of Patent: Mar. 23, 2010

(54) PLUM TREE NAMED 'SWEET MAJESTY'

(50) Latin Name: *Prunus salicina*
Varietal Denomination: Sweet Majesty

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,594

(22) Filed: Dec. 15, 2008

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP2,747 P 6/1967 Garabedian
PP7,503 P 4/1991 Bradford
PP14,220 P2 10/2003 Bradford

*Primary Examiner*—June Hwu

(57) ABSTRACT

The present invention relates to a plum tree and more particularly to a new and distinct variety broadly characterized by a medium size, moderately vigorous, hardy, and very productive tree. Being self-unfruitful, the present variety requires cross pollination from a plum that blooms during the mid to late season. The present variety's abundance of blossoms and pollen entices strong bee activity to facilitate pollination. The fruit matures under the ecological conditions described during late August through early September, with first picking on Aug. 18, 2008, and will hang on the tree for about three more weeks. The fruit is uniformly medium in size, dark purple in skin color, clingstone in type, mostly globose in shape, yellow in flesh color, firm in texture, and very sweet in flavor.

1 Drawing Sheet

Botanical classification: *Prunus salicina.*
Varietal denomination: 'Sweet Majesty'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Sweet Majesty'.

During the 2003 blooming season I placed paper grocery bags over several branches of a 'Purple Majesty' (U.S. Plant Pat. No. 7,503) plum. When the flowers of this tree neared full bloom, I removed one such bag and applied pollen from 'September Yummy' (U.S. Plant Pat. No. 14,220) plum to the visible pistils. Following this pollen application I immediately replaced the bag to keep the flowers isolated from other sources of pollen during the blooming period. After petal fall, I removed the bag and allowed the fruit to mature. Upon reaching maturity the fruit from this plum tree was harvested and the seeds were removed, cracked, stratified and germinated as a group with the label "7P865 BAGS SY". They were grown as seedlings on their own root in my greenhouse and upon reaching dormancy transplanted to a cultivated area of my experimental orchard located near Le Grand, Calif. in Merced County (San Joaquin Valley). During the summer of 2006 the claimed variety was selected by me as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Purple Majesty' (U.S. Plant Pat. No. 7,503) plum by being self-unfruitful and by producing fruit that is dark purple in skin color, that is yellow to orange yellow in flesh color, that is clingstone in type, that is firm in texture, and that is very sweet in flavor, but is distinguished therefrom by producing fruit that is larger in size, globose instead of oblate in shape, and that matures about fifty days later.

The present variety is similar to 'September Yummy' (U.S. Plant Pat. No. 14,220) plum by being self-unfruitful and by producing fruit that ripens in the late season, that is firm in texture, that is mostly globose in shape, that is mostly yellow in flesh color, and that is very good in flavor, but is distinguished therefrom by producing fruit that is dark purple in skin color instead of red, that is clingstone instead of semi-freestone, and that matures about fifty days earlier. It is to be noted that the patent for 'September Yummy' plum describes a first pick date of Sep. 10, 2002. Since the filing of that patent, it has been established that the average commercial first pick date is closer to October 10th.

The present variety is similar to 'Angeleno' (U.S. Plant Pat. No. 2,747) plum by being self-unfruitful and by producing fruit that is dark purple to black in skin color, that is clingstone in type, and that ripens in the late season, but is distinguished therefrom by producing fruit that is sweeter in flavor, that possesses and maintains much more juice, that is larger in size, and that matures about ten days earlier.

SUMMARY OF VARIETY

The present plum variety is characterized by a medium size, moderately vigorous, hardy, and very productive tree. Being self-unfruitful, the present variety requires cross pollination from a plum that blooms during the mid to late season. The present variety's abundance of blossoms and pollen entices strong bee activity to facilitate pollination. The fruit matures under the ecological conditions described during late August through early September, with first picking on Aug. 18, 2008, and will hang on the tree for about three more weeks. The fruit is uniformly medium in size, dark purple in skin color, clingstone in type, mostly globose in shape, yellow in flesh color, firm in texture, and very sweet in flavor.

DRAWING

The accompanying photograph consists of four whole fruits positioned to display the characteristics of the skin color and form, two half fruits divided to reveal the flesh and stone, a cleaned stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif. The fruit description was developed at the state of full ripe on Sep. 10, 2008, on the original tree during its fifth growing season. The flower and bud descriptions were developed during the previous blooming season. All major color code designations are by reference to the Inter-Society Color Council, National Bureau of Standards. Common color names are also used occasionally.

Parentage

Seed parent: 'Purple Majesty' U.S. Plant Pat. No. 7,503.

Pollen parent: 'September Yummy' U.S. Plant Pat. No. 14,220.

Tree

Size: Medium, reaching a height of 13' [3.96 m.] and a spread of 9' [2.74 m.] after five growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming apricot, interspecific, or plum, such as 'September YUMMY' (U.S. Plant Pat. No. 14,220).

Bearing: Regular bearer, with no crop failures observed.

Trunk:

*Size.*—Medium, reaching a maximum diameter of 3¾" [95.3 mm.] after the fifth growing season.

*Texture.*—Shaggy.

*Bark color.*—A Moderate yellowish brown [77. m.yBr] and Dark grayish yellowish brown [81. d.gy.yBr] variegation with Dark reddish brown [44. d.rBr] crevices present.

*Lenticels.*—Approximate Number Per Square Inch: 5. Color: Deep orange yellow [69. deep OY]. Average Size: ⅜" [9.5 mm.]. Shape: Elongated, eye-shaped.

Branches:

*Size.*—Diameter of limb is 2⅝" [66.7 mm.] measured 12" above crotch, 2" [50.8 mm.] measured 12" above first fork.

*Texture.*—Smooth on first and second year wood, increasing roughness with age.

*Color.*—1st Year Wood Topside: Moderate yellowish Brown [77. m.yBr]. 1st Year Wood Underside: Brilliant yellow green [116. brill.YG]. 2nd Year Wood: Strong brown [55. s.Br] with Deep greenish yellow [100. deep gY] permeating through. Older Wood: Grayish brown [61. gy.Br] with Moderate orange yellow [71. m.OY] crevices present.

*Lenticels.*—Number Per Square Inch: More than 60 on second year wood. Color: Light yellowish brown [76. l.yBr]. Average Size: 1/16" [1.6 mm] to 1/32" [0.8 mm.]. Shape: Eye shaped.

Leaves:

*Size.*—Medium. Average Length: 4⅛" [105 mm.]. Average Width: 1½" [38 mm.].

*Arrangement.*—Alternate.

*Thickness.*—Medium.

*Form.*—Elliptical.

*Apex.*—Acuminate.

*Base.*—Acute with an average angle base angle of 60 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ¾" [19.1 mm.]. Average Thickness: 1/16" [1.6 mm.]. Color: Pale yellow green [121. p.YG], often Grayish red [19. gy.R] where exposed to direct sunlight.

*Stipules.*—Number: Up to 2 per leaf at young stage, up to 6 per growing tip, more prevalent in the spring. Average Length: ⅜" [9.5 mm.]. Color: Light yellow green [119. l.YG] becoming Light reddish Brown [42. l.rBr] with age.

*Glands.*—Number: Mostly 2 per leaf. Position: Oppositely positioned at the intersection of the petiole and the leaf blade. Size: Small. Form: Globose. Color: Light yellow green [119. l.YG] becoming Moderate reddish brown [43. m.rBr] with age. Leaf buds: Pointed, medium.

Flower buds:
- *Hardiness.*—Hardy, with respect to central California winters.
- *Diameter.*—Typically 3/16" [4.8 mm.] 1 week before bloom.
- *Length.*—Typically 3/8" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.
- *Average flower diameter.*—15/16" [23.8 mm.].
- *Number of petals.*—Five, no double blossoms observed.
- *Petal shape.*—Oval to circular.
- *Petal margin.*—Entire, slightly wavy.
- *Average petal diameter.*—7/16" [11.1 mm.].
- *Average petal length.*—1/2" [12.7 mm.].
- *Petal apex.*—*Rounded.*
- *Petal base.*—Obtuse.
- *Petal color.*—White [263. White] on both sides.
- *Anther color.*—Strong orange yellow [68. s.OY].
- *Stigma color.*—Light greenish yellow [101. l.gY].
- *Sepal color.*—Light yellow green [119. l.YG] on the outer surface with very slight Light grayish red [18. l.gy.R] toward the edges.
- *Sepal length.*—1/8" [3.2 mm.].
- *Sepal width.*—1/8" [3.2 mm.].
- *Sepal apex.*—Rounded to elliptical to match the width and length.
- *Sepal margin.*—Fairly smooth, with slight serration toward the apex.
- *Average pistil length.*—9/16" [14.3 mm.].
- *Average stamen length.*—1/2" [12.7 mm.].
- *Fragrance.*—Moderate.
- *Pollen production.*—Strong, bee enticing.
- *Bloom density.*—Heavy.
- *Number per cluster.*—2 to 8, average 4.
- *Blooming period.*—Medium to late, two days after 'Santa Rosa' plum (unpatented).
- *Onset of bloom.*—One percent on Mar. 1, 2008.
- *Date of full bloom.*—Mar. 7, 2008.
- *Duration of bloom.*—One to two weeks, dependent on ambient temperature.

FRUIT

Maturity when described: Full ripe, Sep. 10, 2008.
Date of first picking: Aug. 28, 2007.
Date of last picking: Sep. 10, 2007.
Size: Uniform, medium.
- *Average diameter axially.*—2 9/16" [65.1 mm.].
- *Average diameter across cheek plane.*—2 1/2" [63.5 mm.].
- *Average diameter across suture plane.*—2 9/16" [65.1 mm.].
- *Typical weight.*—5.2 ounces [147.4 grams].

Form: Uniform, mostly globose, symmetrical.
- *Longitudinal section form.*—Round.
- *Transverse section through diameter.*—Round.

Suture: An inconspicuous shallow groove extending from the base to just beyond the pistil point.
Ventral surface: Rounded, lipped toward base.
Lips: Equal.
Cavity: Flaring, circular, suture showing on one side.
- *Depth.*—7/16" [11.1 mm.].
- *Breadth.*—1 1/16" [27 mm.].

Base: Slightly truncate, slightly cordate if viewed parallel to the suture.
Apex: Rounded to slightly truncate with a slight bulge just past the apex away from the suture.
Pistil point: An inconspicuous Grayish yellowish brown [80. gy.yBr] dot located at the end of the suture.
Stem: Medium.
- *Average length.*—7/16" [11.1 mm.].
- *Average width.*—1/16" [1.6 mm.].

Skin:
- *Thickness.*—Medium.
- *Surface.*—Smooth.
- *Tenacity.*—Tenacious to the flesh.
- *Astringency.*—Slight.
- *Tendency to crack.*—Non observed (dry season).
- *Color.*—Very dark purplish red [260. v.d.pR] over a Very deep red [14. v.deep R] background with moderate Grayish yellowish brown [80. gy.yBr] freckling on the sides.
- *Bloom.*—Abundant.

Flesh:
- *Color.*—Brilliant yellow [83. brill.Y] near skin blending to Strong orange yellow [68. s.OY] toward the stone.
- *Surface of pit cavity.*—Covered with Deep orange yellow [69. deep OY] broken fibers when twisted away from stone.
- *Amygdalin.*—Moderate.
- *Juice.*—Abundant, rich.
- *Texture.*—Firm, crisp.
- *Fibers.*—Abundant, fine, tender.
- *Ripens.*—Fairly even, slightly earliest at the apex.
- *Flavor.*—A tasty balance of acid and sugar, typically 20 brix.
- *Aroma.*—Very slight.
- *Eating quality.*—Very good.

STONE

Type: Clingstone.
Form: Oval.
Hilum: Narrow, oblong.
Base: Slightly oblique.
Apex: Acuminate.
Sides: Equal.
Surface: Rough throughout.
External color of stone: Moderate brown [58. m.Br] when first removed.
Pit wall color when cracked: Dark yellowish brown [78. d.yBr].
Cavity surface color: Light yellowish brown [76. l.yBr].
Average pit wall thickness: 3/32" [2.4 mm.]
Average width: 11/16" [17.5mm.].
Average length: 1 1/16" [27 mm.].
Average breadth: 3/8" [9.5 mm.].
Tendency to split: Non observed.
Kernel:
- *Form.*—Oval.
- *Skin Color.*—Strong yellowish brown [74. s.yBr] when first removed.
- *Pellicle color.*—Deep yellowish brown [75. deep yBr].
- *Vein color.*—Dark yellowish brown [78. d.yBr].
- *Taste.*—Bitter.
- *Viable.*—Yes.
- *Average width.*—3/8" [9.5 mm.].
- *Average length.*—9/16" [14.3 mm.].
- *Amygdalin.*—Abundant.

Use

Market: Fresh market and long distance shipping.
Keeping quality: Good, fruit quality observed to remain in good condition after 20 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is similar to 'Angeleno' (U.S. Plant Pat. No. 2,747) plum by being self-unfruitful and by producing fruit that is dark purple to black in skin color, that is clingstone in type, and that ripens in the late season, but is distinguished therefrom by producing fruit that is sweeter in flavor, that possesses and maintains much more juice, that is larger in size, and that matures about ten days earlier.

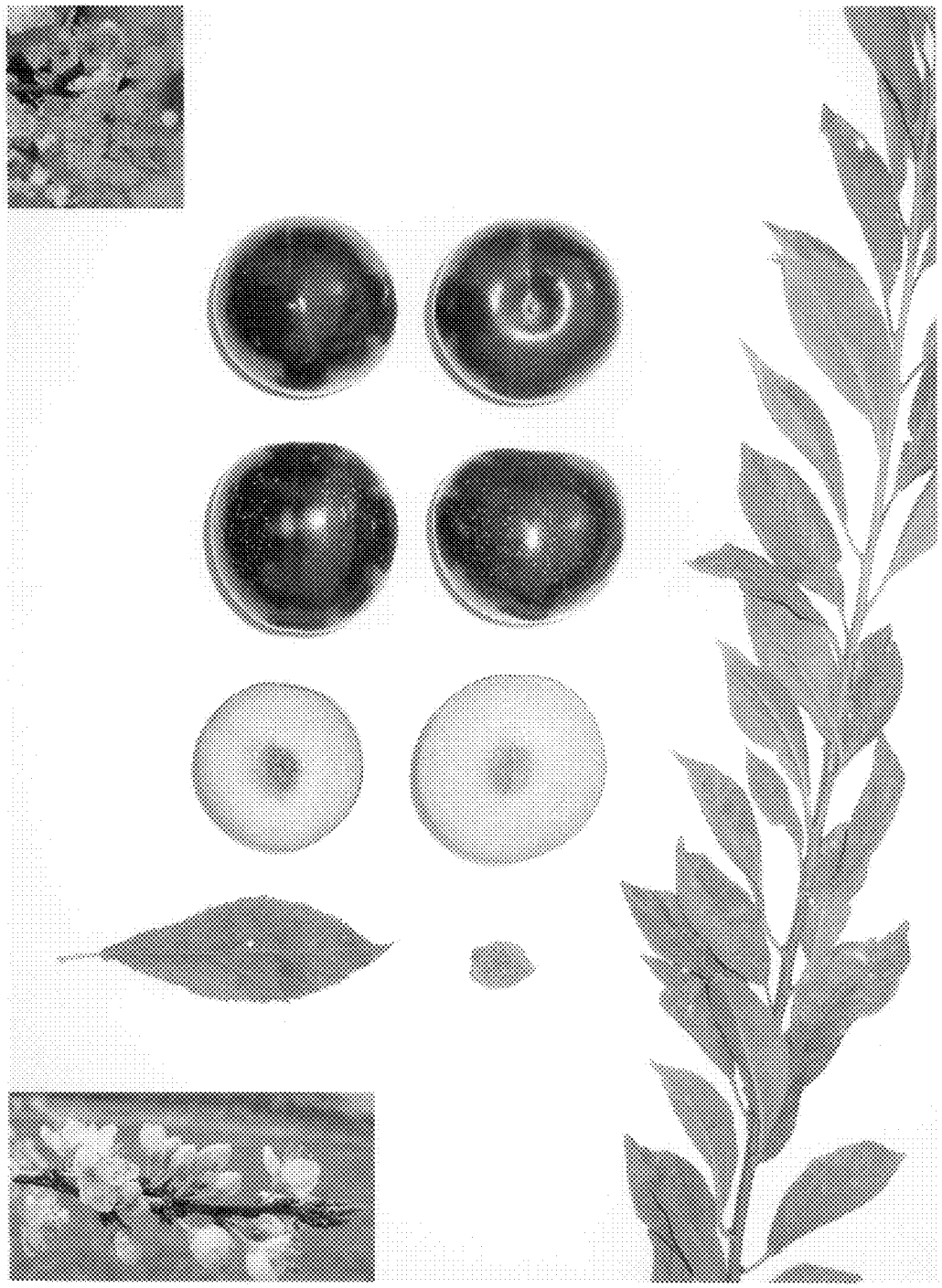

* * * * *